United States Patent [19]

Horn et al.

[11] Patent Number: 4,888,012

[45] Date of Patent: Dec. 19, 1989

[54] INTRAOCULAR LENS ASSEMBLIES

[76] Inventors: Gerald Horn, 74 Golf Rd., Golf, Ill. 60029; Kenneth Spears, 9141 Dr. Korczak Ter., Skokie, Ill. 60076

[21] Appl. No.: 144,318

[22] Filed: Jan. 14, 1988

[51] Int. Cl.[4] .............................................. A61F 2/16
[52] U.S. Cl. ............................................................ 623/6
[58] Field of Search ............................................. 623/6

[56] References Cited

U.S. PATENT DOCUMENTS

| | | | |
|---|---|---|---|
| 4,253,199 | 3/1981 | Banko | 623/6 |
| 4,373,218 | 2/1983 | Schachar | 623/6 |
| 4,409,691 | 10/1983 | Levy | 623/6 |
| 4,424,597 | 1/1984 | Schlegel | 623/6 |
| 4,439,873 | 4/1984 | Poler | 623/6 |
| 4,512,040 | 4/1985 | McClure | 623/6 |
| 4,575,373 | 3/1986 | Johnson | 623/6 |
| 4,585,457 | 4/1986 | Kalb | 623/6 |
| 4,619,662 | 10/1986 | Juergens | 623/6 |
| 4,709,996 | 12/1987 | Michelson | 623/6 |

Primary Examiner—Richard J. Apley
Assistant Examiner—James Prizant
Attorney, Agent, or Firm—James B. Raden

[57] ABSTRACT

An intraocular lens assembly for implantation into a posterior eye chamber is provided having a central lens and an outer ring interconnected therewith. The assembly when implanted is operatively engaged by the ciliary muscle of the eye which causes changes in the focusing power of the lens in order to achieve accommodation.

21 Claims, 2 Drawing Sheets

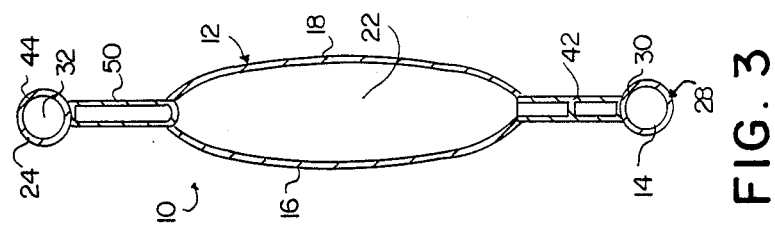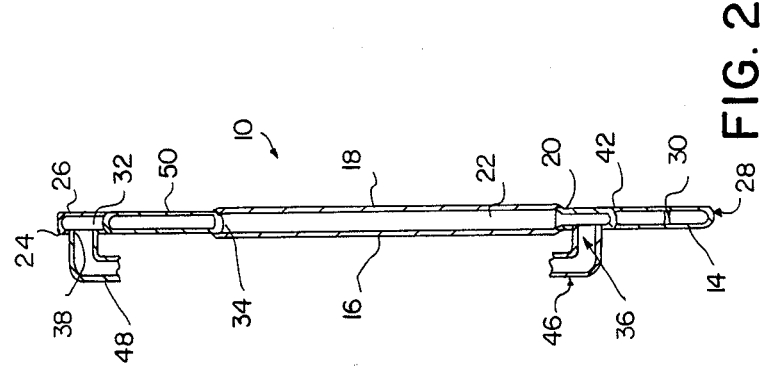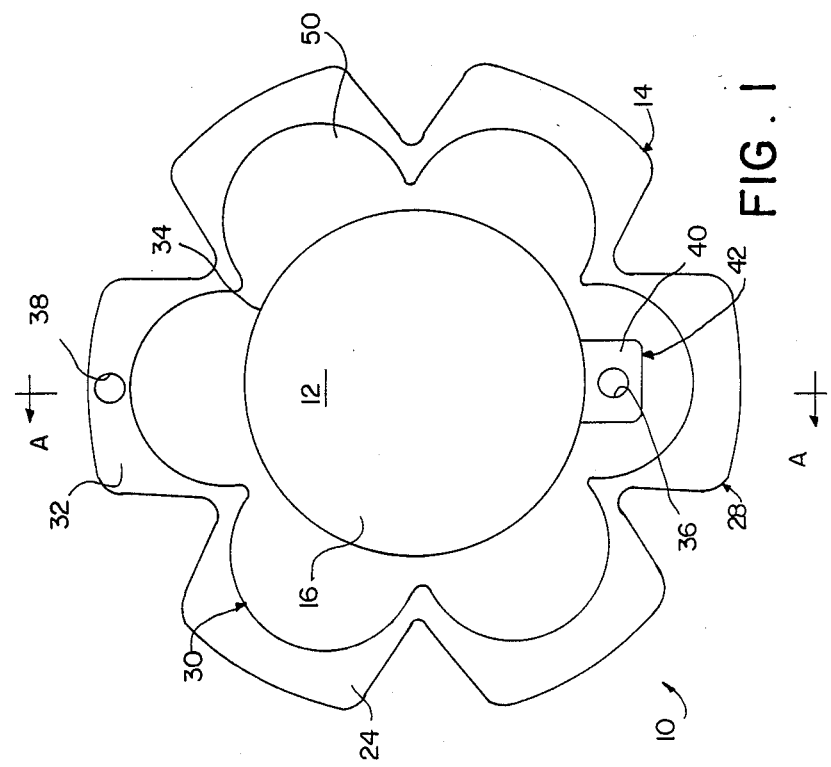

INTRAOCULAR LENS ASSEMBLIES

BACKGROUND OF THE INVENTION

This invention relates to intraocular lens assemblies for implantation into the posterior chamber of a human eye and, more particularly, to accommodating lens assemblies for implantation during cataract eye surgery.

Heretofore, conventional cataract surgery has involved the removal of the normal lens of a human eye and replacement thereof with an artificial intraocular lens assembly which does not have the the ability to change shape for focusing at different distances, as can the normal lens of the eye. The normal lens has the capability of focusing objects in a range of distances which varies from a near point of about 50 millimeters to a far point of infinity. This focusing effect is accomplished by a process known as accommodation. However, the heretofore standard replacement lenses have been fixed focus lenses designed for either distant or close-up vision and have lacked the ability to achieve accommodation. Thus, a patient, having one of these prior lenses implanted during surgery, typically has been required to wear appropriate conventional bifocal or reading glasses thereafter to compensate for the non-accommodating nature of the implant.

U.S. Pat. No. 4,254,509 discloses an intraocular lens structure which is taught to provide properties of accommodation. The lens structure therein includes an optical lens portion which is incapable of changing its curvature since it is formed from a rigid methyl methacrylate-type material such as polymethyl methacrylate ("PMMA"). This rigid, fixed configuration lens portion is supported by haptics which are integrally formed with coplanar oppositely directed feet. The haptics are constructed from a soft, relatively flexible material such as soft hydrogels of hydrophylic type including 2-hydroxyethyl methacrylate ("PHEMA"). These supporting haptics have an archlike configuration, convex side facing the cornea, so that the optic will not touch the iris but will be slightly anterior to it when the structure is implanted in the anterior chamber of the eye. Focusing power of this prior assembly is said to change through anterior movement of the optic resulting from central compressive force exerted on the feet and translated through the soft haptics to the lens upon contraction of the ciliary muscle when the lens is implanted in the anterior chamber of the eye. That is, the patent teaches that central compression of the soft haptics of the lens implanted in the anterior chamber of the eye displaces the lens forward and, thereby, increases the optical power of the system by moving the focusing lens away from the retina. However, it has been found that this system when implanted as taught in the patent does not solve the problem of providing an operationally effective accommodating lens assembly.

A disadvantage of the prior lens assembly is that it is configured for implantation into the anterior chamber of the eye wherein the feet of the haptic supporting the lens are in the anterior chamber angle and, therefore, are effectively in contact with the scleral spur or iris root. As described, the feet of the lens thus positioned in the anterior chamber are pushed centrally during accommodation by an amount sufficient to result in a useful increase in accommodative power. However, it has been found that contraction of the ciliary muscle does not move the scleral spur or iris root centrally or anteriorly. Accordingly, insufficient central movement occurs at the periphery of the anterior chamber to achieve the necessary accommodation with these lens assemblies. Furthermore, to the extend that there is any central displacement of these lens assemblies, less than a millimeter of anterior movement can be achieved in the anterior chamber of the eye when clearance of the iris and cornea are considered. This amount of movement would provide less than about 1 diopter of accommodation utilizing these lens assemblies whereas at least about 3 diopters of accommodation are required to allow focus to go from distance to normal reading vision and about 5 diopters to achieve this degree of accommodation without asthenopia (discomfort resulting from eye strain). Indeed, at least about 8 diopters is preferred to develop an operationally effective accommodating lens system in view of the difficulty in predicting a lens power which would result in ideal distance vision.

SUMMARY OF THE INVENTION

It is an object of the present invention to provide intraocular lens assemblies which avoid the disadvantages inherent in the prior lens assemblies. Specifically, it is a primary object of this invention to provide accommodating lens assemblies for implantation into the posterior chamber of the human eye. Another primary object is to provide accommodating lens assemblies wherein at least about a 3 diopter change in the focusing power of the eye is achieved and, preferably, the degree of accommodation achieved is at least about 5 diopters, most preferably at least about 8 diopters.

In accordance with the present invention, intraocular lens assemblies are provided which utilize the ciliary muscle to produce changes in lens curvature and geometry whereby accommodation is achieved. Specifically, the assemblies of this invention include ring structures which support deformable central lens structures. The ring structures comprise outer ring members having web members extending therefrom. These web members are connected at there distal ends to the central lens structures or are formed integral with and as a unitary extension of the central lens. The lens structures are constructed from elastic materials which have the ability to be extended or compressed when appropriate radial pressure is applied thereto and to essentially return to their original shapes when such pressure is relaxed. These lens structures act as the deformable focusing or optic portions of the assemblies.

The outer ring members of the ring structures are adapted to engage with and to be compressed by contraction of the ciliary muscle after implantation of the assembly into the eye whereby tension on the optic is relaxed to enable adjustment of the curvature and geometry of the central lens to achieve accommodation. More specifically, as radial tension transmitted from the ring to the central lens is relaxed, the lens contracts its diameter from its original minimum focusing or non-accommodative shape causing an increase in the central thickness of the lens thereby increasing curvature of the lens and the focusing power thereof. Subsequently, as outer ring tension is increased on the lens via muscle relaxation, the lens will expand its diameter as a function of the tension exerted thereon so that the shape of the lens will revert to the original non-accommodative form as the tension applied thereto returns to the initial level.

Furthermore, in preferred embodiments of the present invention, the assemblies are specially designed and constructed to allow safe and efficient implantation or insertion thereof into the posterior chamber of an eye through a significantly smaller incision than has been possible heretofore. In this regard, it is preferred to insert an inflatable assembly while it is in a noninflated or collapsed state. However, it is within the purview of this invention to provide an assembly wherein either the lens or the outer ring member or both the lens and the outer ring are either pre-molded or are fully or partially inflated by injecting highly deformable material therein prior to implantation and are, thus, implanted in a fully or partially inflated state.

After the structure has been implanted into the posterior chamber with the lens and outer ring structures fully expanded either prior to or after insertion, the outer ring member will be in operative contact with the ciliary muscle at the ciliary epithelium at or just posterior to the ciliary sulcus. In this position, the ring is in generally circumferential contact or near contact with the muscle so that a substantial fraction of the muscle diameter change resulting from contraction of the muscle can be converted into essentially uniform circumferential change of the central deformable lens through the connections between the ring structure and the lens structure to accomplish essentially uniform deformation of the lens and increased as well as adjustable focusing power as previously described.

BRIEF DESCRIPTION OF THE DRAWINGS

Other objects features and advantages of the accommodating, posterior chamber implant lens assemblies of this invention will become apparent from the following detailed description of preferred embodiments taken in conjunction with the drawings wherein:

FIG. 1 is a top plan view of an intraocular lens assembly of this invention;

FIG. 2 is a cross-sectional view taken along line A—A of FIG. 1 showing the lens assembly prior to implantation in a collapsed state with cannulae attached to the fill ports for inflating the lens and the ring structures;

FIG. 3 is a cross-sectional view taken along line A—A of FIG. 1 showing the lens assembly after inflation with the cannulae removed;

DETAILED DESCRIPTION OF THE DRAWINGS

Figure 4:
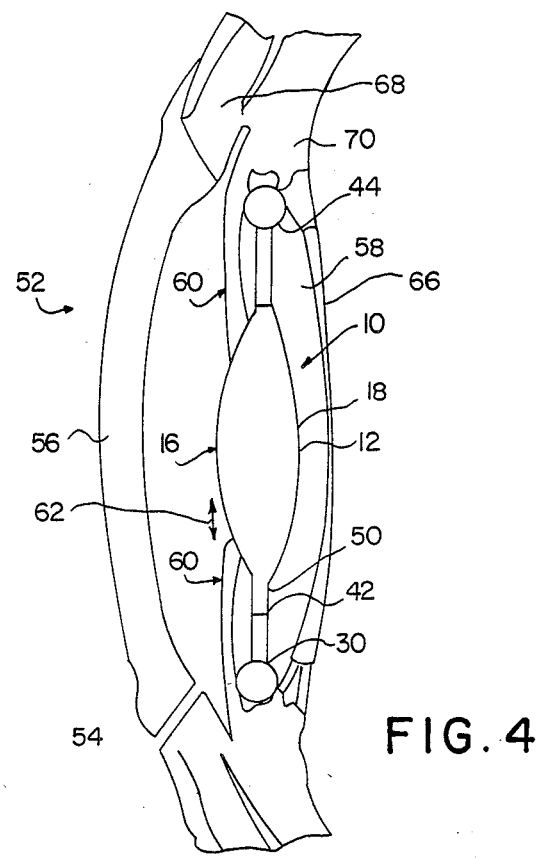
FIG. 4 is a perspective view of the lens assembly of FIG. 1 in an inflated state implanted into the posterior chamber of a human eye.

FIG. 1 illustrates an intraocular lens assembly 10 adapted for implantation into the posterior chamber of the human eye. The structure comprises a central optical lens structure 12 and a supporting multi-lobe ring structure 14. The lens structure 12 is formed by bonding or sealing the circumferential edges of two juxtaposed, congruent circular sheets or membranes 16 and 18 of soft, elastic material such as a silicone rubber, polyurethane rubber or another polymeric elastomer which is optically clear and biologically inert. However, as best illustrated in FIG. 2, an edge section between the membranes 16 and 18 is left unsealed to provide a passage 20 into a chamber 22 formed intermediate the anterior and the posterior membranes 16 and 18, respectively, to enable inflation of the lens structure as will be described in greater detail hereinafter.

The ring structure 14 includes two juxtaposed flat, expansible members 24 and 26, each formed from a strong, thin material such as a polyimide or a polyester polymeric sheet. The members 24 and 26 are shaped in congruent multi-lobe configurations and are bonded or sealed together along their peripheral edge 28 as well as along an intermediate lobed boundary line 30 whereby an intermediate fill chamber 32 is formed between the sealed edge 28 and the boundary line 30.

Optionally, the membranes 16, 18 of the lens structure 12 and the members 24, 26 of the ring structure 14 may be formed from any suitable discrete elastic materials or they may all be formed from a single elastic material. If all of the elements 16, 18, 24 and 26 are constructed from a single material, it may be preferable to vary the thickness of the portion of the elastic material utilized to form the membranes 16, 18 of the lens structure 12 as compared with the thickness of the same material utilized to form the members 24, 26 of the ring structure 14 for certain applications. Thus, exemplary of the options available for constructing the assembly 10 herein, membranes 16, 18 and members 24, 26 may be formed from the same elastic material; or membrane 16 and member 24 may be formed from one elastic material and membrane 18 and member 26 from another; or elements 16, 18, 24 and 26 may all be formed fom different elastic materials; or membranes 16, 18 may be formed from one elastic material and members 24, 26 from another elastic material, etc., at the discretion of the manufacturer. Likewise, thickness of the component parts and sections thereof may be selected at the option of the manufacturer.

It should be further noted that bonding or sealing of the various piece parts referenced herein may be accomplished by any suitable means such as by gluing or welding. This gluing or welding and, in addition, the cutting of the pattern for the structure 14 may be performed with a focused laser or electron beam.

As illustrated in FIG. 1, the ring structure 14 includes a central hole 34 which is either formed initially in the members 24 and 26 or which may be cut out subsequent to joinder thereof. The circular lens structure 12 is positioned to cover the hole 34 and is affixed to the circumferential edges of the ring structure 14 surrounding the hole 34 by any appropriate means such as gluing with the passage 20 of the lens 12 being aligned in a manner discussed hereinafter to enable inflation of the lens. However, it should be recognized that the lens structure 12 and the ring structure 14 may optionally be fabricated from a single elastic material by varying the thickness of the different functional regions of the assembly 10. With such an integral construction, the lens 12 and the ring structure 14 are formed coextensively so that an additional affixing step is not required.

After inflation, the thickness of the lens 12 will vary depending on the amount of material injected therein to inflate the structure. The diameter of the lens also will vary depending on the particular tension applied to the central lens 12 as previously discussed. However, in its original non-accommodative shape, a lens diameter of about 5–8 mm. is preferred and, a diameter of about 6.5–7.5 mm. is most preferred.

The anterior member 24 of the ring structure 14 includes two openings 36 and 38 which provide fill ports for injecting materials such as viscous fluids or fluid compositions which are gels or cure with a gel-like or elastomeric consistency into the assembly 10 to inflate it. These openings 36, 38 are positioned in the multi-lobe structure 14 to maintain the spherical arrangement of the lens assembly 10. The openings 36 and 38 optionally can be covered with a fill tube interface or septum (not shown) of varying design affixed to the flat surface to retain material therein after injection and to prevent leakage.

As illustrated in FIG. 2, flexible tubes or cannulae 46 and 48, which are formed from either metal or flexible polyimide or polyester tubing, are attached to the openings 36 and 38 to facilitate connection of the openings to a syringe or other injection device for introducing injectible materials into the assembly 10 for purposes of inflating the assembly. Specifically, the opening 36 is positioned in anterior member 24 and communicates directly with a passage section 40 formed by sealing or bonding members 24 and 26 together along a boundary line 42. The passage section 40 is positioned to interconnect with passage 20 which opens into chamber 22 in leans structure 12 so that material injected through cannula 46 into opening or fill port 36 will be transported solely through passage section 40 and passage 20 into chamber 22 of lens 12 whereby the lens structure 12 will be inflated. The opening 38 in anterior member 24 communicates directly with fill chamber 32 of ring structure 14 so that injection of material through cannula 48 and opening or fill port 38 will result in the inflation of the fill chamber 32 whereby, as best illustrated in FIG. 3, an outer ring 44 will be formed as a result of the introduction of the injectible material therein. Intermediate this inflated outer ring 44 and inflated lens structure 12, a web section 50 is defined by that section of the multi-lobe ring structure 14 which is sealed off from inflation through the openings 36 and 38. Thus, as illustrated, the web 50 is attached to and extends radially inwardly of the outer ring 44 and is connected at its distal end to the lens 12.

In FIG. 4, the lens assembly 10 is shown implanted in an eye 52. As illustrated, the assembly 10 has been inserted through a small incision 54 made in the cornea 56 of the eye 52 into the posterior chamber 58 of the eye 52 posterior to the iris 60. In the surgical procedure employed for implanting the assembly 10, the natural lens is first removed from the pupil 62 of the eye 52. Then, the assembly 10 is inserted through incision 54 either in a collapsed state (i.e., with the len structure 12 and the multi-lobe ring structure 14 uninflated) with cannulae 46 and 48 attached or in a fully or partially inflated state. Assuming that the assembly 10 is inserted with an initially collapsed outer ring 44 of the ring structure 14 implanted posterior to the iris 60 and with an uninflated lens 12. Then, after implantation, the assembly 10 is inflated by injecting appropriate injectible material into the outer ring 44 and the lens 12 whereby the assembly 10 will expand so that the outer ring 44 will seat in the ciliary sulcus region 70 adjacent ciliary muscle 68 and will be in operative engagement with the muscle 68. The assembly 10 is inflated sufficiently after implantation so that the outer ring 44 will exert a stretching tension on the lens 12 with this stretching tension being transmitted to the lens 12 via the web 50.

In a preferred embodiment of this invention, the lens assembly 10 is inflated after implantation by first injecting the injectible material into the outer ring 44 as previously detailed so that a diameter of the ring 44 is achieved sufficient to essentially match the circumference of the sulcus region 70 adjacent to the ciliary muscle 68. Then, the lens 12 is inflated as previously discussed by injecting a viscous fluid or gel type polymer into the chamber 22 in lens 12. However, in alternative preferred embodiments of this invention, the outer ring 44 and/or the lens 12 is either fully or partially inflated prior to implantation by injecting therein a material which is highly deformable and which will compact sufficiently to enable the assembly to be inserted through an extremely small incision into the posterior chamber of the eye.

With regard to the injectible material, the ring structure 44 and center lens structure 12 formed from elastic membranes 16 and 18 may be injected with a composition which is selected independent of the injectible material selected for injection into the ring structure 44 thereby, enabling flexibility in construction and application. For example, the desired focusing power of the lens 12 may be controlled simply by controlling the volume or the index of refraction of the material injected into the lens 12 or the operability of the ring 44 can be altered by controlling the volume or the cure properties of the material injected into the ring 44. As previously noted, selection of a suitable highly deformable injection material for introduction into the assembly 10 is instrumental in enabling provision of an implant which may be inserted in an inflated state into the posterior chamber of the eye.

The intraocular lens 10, functions to provide accommodation by utilizing the contractions of the ciliary muscle 68 in much the same manner as the human eye employs these muscle actions on the natural lens. Specifically, after the assembly 10 is implanted, muscle pressure is applied to the ring structure 44 which is positioned in operative engagement with muscle 68 and which applies tension on elastic center lens 12 via a web 50.

In operation, the muscle 68 compresses the outer ring structure 44 which then allows the stretching tension transmitted from the outer ring 44 to the lens 12 via the web 50 to relax. This relaxation of the tension thereon enables the lens 12 to deform in an essentially uniform manner into a reduced diameter with increased lens curvature providing increased focusing power whereby accommodation is achieved.

Thus, in an exemplary embodiment of this invention, the dimension of the outer ring 44 implanted in the eye 52 matches the maximum muscle diameter of the surrounding ciliary muscle 68 so that the lens 12 is stretched to its maximum diameter. This maximum lens diameter will provide minimum focusing power. However, muscle contraction will allow the diameter of the lens 12 to slightly reduce as a result of the relaxation of the tension exerted by the web 50 on the lens 12 as transmitted through the outer ring 44. Accordingly, the inherent elasticity of the membranes forming the lens 12 will cause the lens structure 12 to symmetrically deform by a radial increment of at least about 0.1 mm. as a result of displacement of the viscous fluid or gel therein upon release of this applied tension and the lens focusing power will increase by an amount of at least about 3 diopters. In a most preferred embodiment of this invention the lens deforms by a radial increment of at least about 0.2 mm. resulting in a change of focusing power of at least about 8 diopters.

Figure 5:
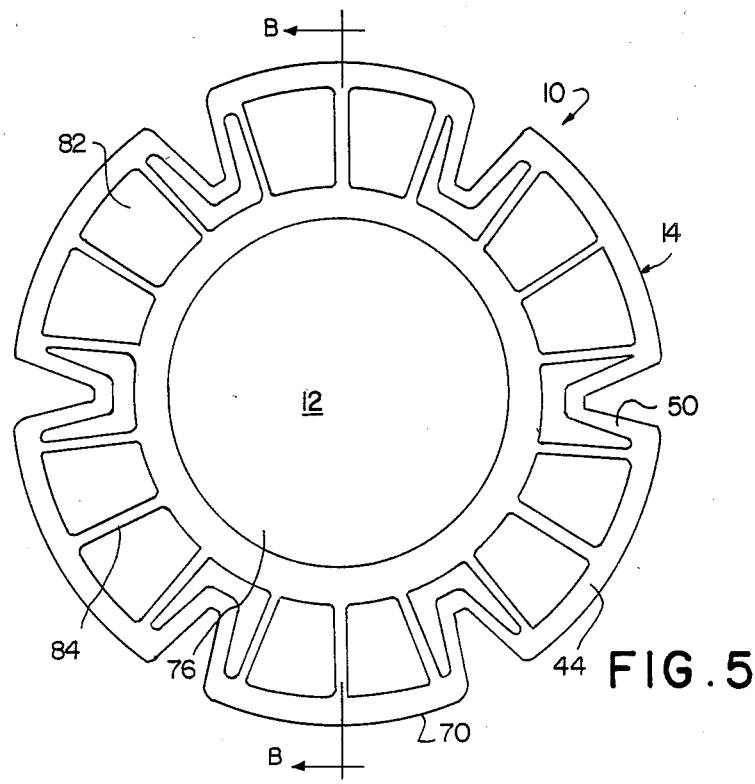
FIG. 5 is a top plan view illustrating another embodiment of an intraocular lens assembly of this invention.
Figure 6:
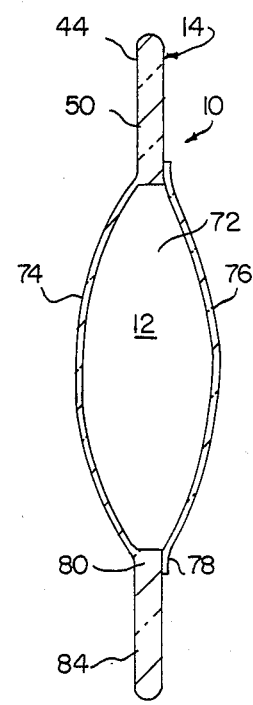
FIG. 6 is a cross-sectional view taken along line B—B of FIG. 5 showing the lens assembly in a fully expanded condition.

FIGS. 5-6 illustrate another preferred embodiment of an intraocular lens implant of this invention wherein like reference numerals denote like elements of structure to those illustrated in FIGS. 1-4. As shown in FIGS. 5-6, a premolded disk 70 is provided having a circular cavity or depression 72 formed centrally therein. This central cavity 72 is inset into the surface of the disk 70 to a depth which is slightly less than the total thickness of the disk 70 so that a thin, optically clear membrane 74 is formed centrally in the remaining surface of the disk 70 opposite the open side of the cavity 72. A separate thin, optically clear circular sheet or membrane 76 is bonded, glued or otherwise affixed in sealing engagement over the open side of the cavity 72 by attaching a circumferential edge 78 of the membrane 76 to a rim section 80 circumferentially surrounding the cavity 72 in the premolded disk 70.

Once the membrane 76 is attached to the disk 70 in sealing engagement, the assembly 10 is completed with the central lens 12 being formed in the disk 70 by the cavity 72 enclosed by the membranes 74 and 76 and the ring structure 14 including outer ring 44 and web member 50 which interconnects the lens 12 and the outer ring 44 being provided by the surrounding portion of the disk 70 concentric to the circular central cavity 72. As best illustrated in FIG. 5, the ring structure 14 in this embodiment is in a multi-lobe configuration although shape and arrangement of this structure is a matter of choice.

The disk 70 with the membrane 74 formed integrally therewith can be fabricated from any suitable elastomeric material such as a silicone rubber and the method of formation can be by casting or spin casting with a mold which can be fashioned to create various thicknesses throughout the surface of the disk 72 or in order to achieve special shapes and/or cut-outs therein. For example, as best illustrated in FIGS. 5, it can be seen that the ring structure 14 in disk 70 in the depicted embodiment includes cut-outs 82 which are formed in the section of the disk 70 corresponding to the web member 50 so that the cut-outs 82 are interspersed between strips of webbing 84 which are employed to operatively interconnect the outer ring 44 with the central lens 12. Optionally, the initial molded disk 70 may not include these cut-outs 82 and, if desired, they may be formed later in the disk 70 by employing an additional cutting step. The details of the pattern of the cut-outs 82, if any, utilized in the assemblies 10 depend on various factors such as the elasticity of the material forming the disk 70 and the thickness of the various functional regions of the assembly 10.

Thin circular membrane 76 which is bonded to the open side of the central cavity 72 of disk 70 to form the enclosure for central lens 12 may be formed by casting or spin casting a fluid which can be cured to produce an elastomeric material such as silicone rubber. The enclosed central lens 12 may be inflated into fully expanded condition by the injection of a suitable material such as a viscous fluid or a fluid composition which is a gel or cures with a gel-like or elastomeric consistency into the cavity 72. Introduction of the injectible material into the lens 12 may be accomplished employing any suitable technique such as by injecting the material through canulae formed in the surface of either membrane 74 or 76. Additionally, if desired, the injectible material may be introduced into cavity 72 by injecting the material with a hypodermic needle through the membrane 74 or 76.

The assembly 10 illustrated in FIGS. 5-6 operates in a similar manner to the embodiment of this invention illustrated in FIGS. 1-4. That is, after implantation, the outer ring member 44 of the ring structure 14 is positioned in operative engagement with the ciliary muscle of the eye. The outer ring 44 transmits radial tension to the central lens 12 via the strips 84 which comprise the web member 50 in order to stretch the lens 12 radially outwardly and, upon contraction of the muscle, the outer ring 44 is compressed so that the radial tension transmitted from the outer ring 44 to the lens 12 via the web 50 is relaxed enabling the central lens 12 to essentially uniformly deform about its circumference and to alter its curvature.

In a further preferred embodiment of this invention, the lens 12 as well as the ring structure 14 is pre-molded rather than being expanded or inflated by injection of injectible material therein. For example, such an assembly can be produced by molding a disk 70 with a central circular hole concentrically positioned within a ring structure 14. A lens 12 is molded as a separate circular member of soft, elastomeric material with an outer circumference less than the diameter of the hole in the disk 70. The integral lens 12 then is positioned inside the hole in the disk 70 and the ring structure 14 of the disk 70 is compressed to match the outer circumference of the lens 12 and the outer circumference of the lens 12 is affixed to the inner circumference of the ring structure 14. After attachment is completed and the assembly 10 is allowed to assume its natural state, the ring structure 14 stretches the central lens 12 to a large diameter having a lens curvature different than the curvature of the lens 12 as originally molded in view of the tension applied thereto by the ring structure 14. Upon relaxation of this tension, the assembly 10 operates to achieve an alternate lens curvature as detailed above.

While specific embodiments of this invention have been shown and described herein, it will be clear to those skilled in the art that changes and modifications may be made without departing from the spirit and scope of the invention in its broadest aspects and the following claims are intended to cover all such changes and modifications as fall within the true spirit and scope of the invention.

What is claimed is:

1. An intraocular lens assembly for implantation into the posterior chamber of a human eye in operative engagement with a circumferentially extending ciliary muscle of said eye comprising a central lens supported by a ring structure, said ring structure including a compressively deformable outer ring member having a web member extending radially inwardly of said outer ring member, said web member being connected at its distal end to said central lens, said outer ring member being adapted to apply a circumferentially continuous force to said central lens via said web member when said muscle is in a relaxed condition to stretch said central lens radially outwardly after implantation, said outer ring member being further adapted to operatively and abuttingly engage said circumferentially extending muscle after implantation so that said outer ring is compressed by said muscle upon contraction of the muscle to relax said force applied by said outer ring member to said central lens via said web member to enable said central lens to essentially uniformly deform about its circumference and alter its curvature.

2. The intraocular lens assembly of claim 1 wherein said central lens deforms by a radial increment of at lest about 0.1 mm. and at least about a 3 diopter change in the focusing power of said eye is achieved.

3. The intraocular lens assembly of claim 2 wherein said radial increment is at least about 0.2 mm. and said change in focusing power is at least about 8 diopters.

4. The intraocular lens assembly of claim 1 wherein the central lens is inflated by injecting therein a viscous fluid or a fluid composition which is a gel or cures with a gel-like or an elastomeric consistency.

5. The intraocular lens assembly of claim 1 wherein the central lens is molded from an elastomeric material prior to implantation.

6. The intraocular lens assembly of claim 1 wherein the outer ring member is molded from an elastomeric material prior to implantation.

7. The intraocular lens assembly of claim 1 wherein the outer ring member and the web member of said ring structure are formed in a multi-lobe configuration.

8. The intraocular lens assembly of claim 1 wherein said central lens and said ring structure including said outer ring member and said web member are formed from a single elastic material.

9. An intraocular lens assembly for implantation into the posterior chamber of a human eye in operative engagement with a circumferentially extending ciliary muscle of said eye comprising a central lens supported by a ring structure, said ring structure including an outer ring member having a web member extending radially inwardly of said outer ring member, said web member being connected at its distal end to said central lens, said outer ring member transmitting tension to said central lens via said web member to stretch said central lens radially outwardly after implantation, said outer ring being positioned to operatively engage said circumferentially extending muscle after implantation so that said outer ring is compressed by said muscle upon contraction of the muscle whereby said tension transmitted from said outer ring member to said central lens via said web member is relaxed enabling said central lens to essentially uniformly deform about its circumference and alter its curvature, and wherein the outer ring is inflated by injecting therein a viscous fluid or a fluid composition which is a gel or cures with a gel-like or an elastomeric consistency.

10. An accommodating lens assembly comprising an essentially circular central lens adapted for implantation into an eye, said lens being operatively interconnected to means for exerting a radially outwardly extending tension on said lens after implantation so that said lens is stretched radially outwardly into a nonaccommodative shape and for relaxing said tension exerted on said lens to enable said lens to contact its diameter and thereby change curvature in order to increase focusing power and to achieve accommodation, said means for exerting tension on said lens and for relaxing said tension comprising a ring structure, said ring structure including an inflatable outer ring member.

11. An intraocular lens assembly comprising an essentially circular and elastically deformable central lens and a compressively deformable outer ring member circumscribing said lens, said assembly being adapted for implantation into an eye in a manner such that compressive force is applied to said outer ring member when muscles of the eye contract and such compressive force is absent when said muscles are relaxed, said outer ring member being adapted to abuttingly engage said muscles, said lens being operatively interconnected to said outer ring member so that, after implantation, when said compressive force on said outer ring member is absent, said outer ring member exerts a radially outwardly extending force on said lens whereby said lens is stretched radially outwardly and, when said compressive force is applied to said outer ring member and said outer member is compressively deformed, said force exerted on said lens by said outer member is relaxed to enable said lens to contract its diameter and thereby change curvature in order to increase focusing power and to achieve accommodation.

12. The accommodating lens assembly of claim 11 wherein said ring structure includes an outer ring member molded from an elastomeric material.

13. The accommodating lens assembly of claim 11 wherein said ring structure includes an outer ring member and a web member formed intermediate said central lens and said outer ring.

14. An accommodating lens assembly for implantation into a posterior chamber of an eye in engagement with a circumferentially extending ciliary muscle of said eye comprising a ring structure supporting an inflatable central lens structure, said ring structure including an inflatable outer ring member having web members extending therefrom, said web members being connected to said central lens structure at their distal ens, said lens structure being formed of an elastic material and acting as a deformable focusing portion of said assembly, said outer ring member being adapted to engage with and to be compressed by contractions of said ciliary muscle after said assembly is implanted in said eye whereby tension on said deformable lens structure is relaxed enabling adjustment of the curvature and geometry of said lens to achieve accommodation.

15. The accommodating lens assembly of claim 14 wherein said central lens structure comprises two expansible, congruent circular membranes sealed together along their circumferential edges except for an edge section which is left unsealed to provide a passage for introduction of material into a space between said membranes to inflate said lens structure.

16. The accommodating lens assembly of claim 15 wherein said membranes are formed from an elastic material selected from the group consisting of silicone rubber, polyurethane rubber and mixtures thereof.

17. The accommodating lens assembly of claim 15 wherein said inflate material employed to inflate said lens structure is selected from the group consisting of viscous fluids, fluid compositions which are gels, fluid compositions which cure with a gel consistency and mixtures therof.

18. The accommodating lens assembly of claim 14 wherein said ring structure if formed from two expansible members shaped in congruent multi-lobe configurations, said two members being sealed together along peripheral edges and along an intermediate boundary line to form a fill chamber between said sealed edges and said boundary line which comprises the inflatable outer ring member of said ring structure.

19. The accommodating lens assembly of claim 18 wherein an opening is formed in a surface of one of the two expansible members, said opening communicating with said fill chamber for introduction of material into said chamber to inflate said outer ring member.

20. The accommodating lens assembly of claim 18 wherein said expansible members are formed from polyimide and polyester polymers.

21. The accommodating lens assembly of claim 18 wherein said material employed to inflate said outer ring member is selected from the group consisting of viscous fluids, fluid compositions which are gels, fluid compositions which cure with a gel consistency and mixtures therof.

* * * * *